(12) United States Patent
Williams et al.

(10) Patent No.: US 12,127,889 B2
(45) Date of Patent: Oct. 29, 2024

(54) FORCE LIMITING MECHANISM FOR SURGICAL INSTRUMENTS

(71) Applicant: Conmed Corporation, Largo, FL (US)

(72) Inventors: Mason Williams, Centennial, CO (US); Michael L. Koltz, Jr., Aurora, CO (US)

(73) Assignee: Conmed Corporation, Largo, FL (US)

(*) Notice: Subject to any disclaimer, the term of this patent is extended or adjusted under 35 U.S.C. 154(b) by 248 days.

(21) Appl. No.: 17/631,008

(22) PCT Filed: Jul. 28, 2020

(86) PCT No.: PCT/US2020/043864
§ 371 (c)(1),
(2) Date: Jan. 28, 2022

(87) PCT Pub. No.: WO2021/021803
PCT Pub. Date: Feb. 4, 2021

(65) Prior Publication Data
US 2022/0273390 A1    Sep. 1, 2022

Related U.S. Application Data

(60) Provisional application No. 62/881,078, filed on Jul. 31, 2019.

(51) Int. Cl.
*A61B 90/00* (2016.01)
*A61B 17/29* (2006.01)
(Continued)

(52) U.S. Cl.
CPC .......... *A61B 90/03* (2016.02); *A61B 17/2909* (2013.01); *A61B 18/1445* (2013.01);
(Continued)

(58) Field of Classification Search
CPC ................ A61B 17/2909; A61B 90/03; A61B 2090/033; A61B 2018/00404
See application file for complete search history.

(56) References Cited

U.S. PATENT DOCUMENTS 7,597,693 B2 * 10/2009 Garrison ............ A61B 18/1445
606/51
7,621,927 B2    11/2009 Messerly et al.
(Continued)

FOREIGN PATENT DOCUMENTS

WO    2016/057281    4/2016

OTHER PUBLICATIONS

International Search Report Form PCT/ISA/220, International Application No. PCT/US2020/043864 pp. 1-16, Dated Sep. 25, 2020.
(Continued)

*Primary Examiner* — Robert F Long
*Assistant Examiner* — Xavier A Madison
(74) *Attorney, Agent, or Firm* — Bond, Schoeneck & King, PLLC; David L. Nocilly

(57) ABSTRACT

A force limiting apparatus for a surgical instrument to prevent too much force being applied to the jaws of the instrument. The instrument has a body with a drive shaft coupled to a pair of jaws, a bearing tube secured to the drive shaft, and a pair of tracks carrying a pivot pin that is biased into one end of the track. A lever is coupled to the pivot pin and abuts the bearing tube to move the bearing tube and close the jaws when squeezed by a user. If the lever is over actuated, the pivot pin will slide along the track against the bias of the spring assembly with the lever pivoting about the bearing tube rather than the pivot pin. As a result, the additional movement of lever does not result in any addition force being transmitted to the drive shaft via the bearing tube.

5 Claims, 10 Drawing Sheets

(51) Int. Cl.
*A61B 18/14* (2006.01)
*A61B 18/00* (2006.01)

(52) U.S. Cl.
CPC .................. *A61B 18/1482* (2013.01); *A61B 2018/00404* (2013.01); *A61B 2018/0063* (2013.01); *A61B 2090/033* (2016.02)

(56) References Cited

U.S. PATENT DOCUMENTS

| | | | |
|---|---|---|---|
| 8,562,598 | B2 | 10/2013 | Falkenstein et al. |
| 9,113,940 | B2 * | 8/2015 | Twomey ............... A61B 17/295 |
| 2009/0248007 | A1 | 10/2009 | Falkenstein et al. |
| 2019/0105096 | A1 | 4/2019 | Elliott et al. |

OTHER PUBLICATIONS

Translated Chinese First Office Action, App. No. 202080055906.7, dated Dec. 27, 2023, pp. 1-16.

* cited by examiner

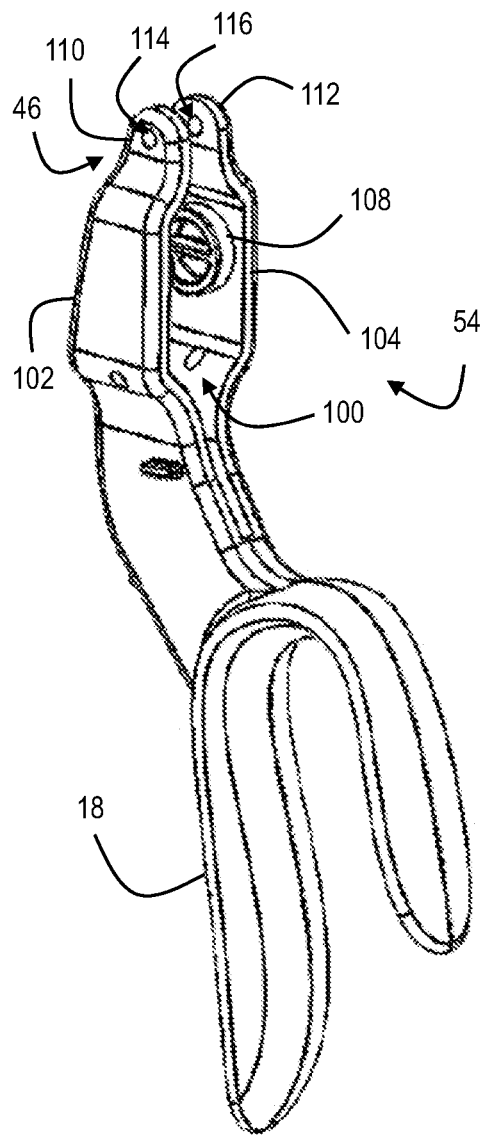
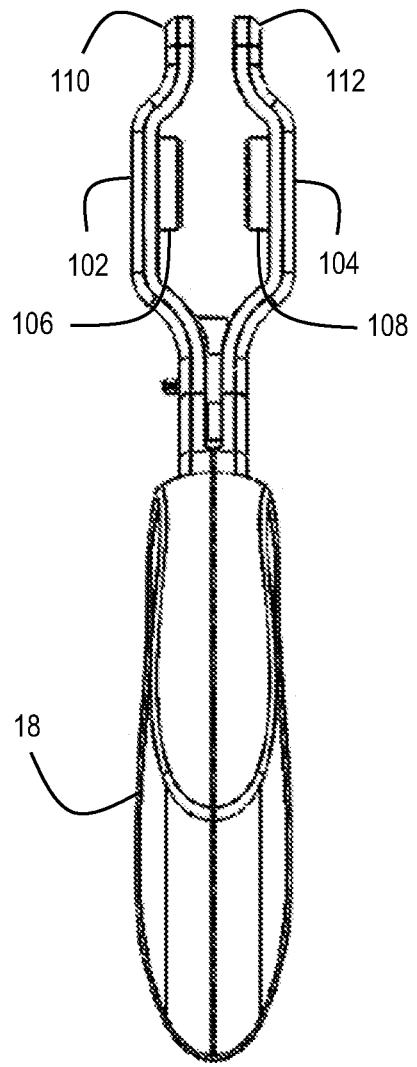
FIG. 7A
FIG. 7B

FORCE LIMITING MECHANISM FOR SURGICAL INSTRUMENTS

CROSS-REFERENCES TO RELATED APPLICATIONS

This application is a national stage application under 35 U.S.C. 371 based on international patent application PCT/US20/43864 filed on Jul. 28, 2020, which claims priority to U.S. Provisional Patent Application Ser. No. 62/881,078, filed on Jul. 31, 2019, the entireties of which are incorporated herein by reference.

BACKGROUND OF THE INVENTION

1. Field of the Invention

The present invention relates to surgical instruments and, more specifically, to a force limiting mechanism for limiting the amount of force applied to the jaws of an electrosurgical instrument.

2. Description of the Related Art

Electrosurgical vessel sealers are used for the occlusion of blood vessels and halting of bleeding during surgical procedures. The electrodes of the vessel sealer are carried by a pair of opposing jaws and interconnected to an electrosurgical generator that can selective supply radiofrequency (RF) energy to the electrodes. A user may close the jaws around a vessel to be sealed by squeezing a lever associated with a handle assembly. The vessel may then be sealed by supplying the RF energy to the clamped vessel. A moveable blade may be additionally incorporated into the jaws for cutting of the sealed blood vessel along an intermediate portion of the seal created by the energized electrodes in response to user activation of a second trigger.

One problem that arises in the use of electrosurgical vessel sealers is the user applying too much force to the jaw closing lever, which can result in breakage of the device. Accordingly, there is a need in the art for an approach that can limit the amount of force that a user can apply to the jaws via the handle lever.

BRIEF SUMMARY OF THE INVENTION

The present invention prevents a user from applying too much force to the jaws by changing the pivoting of the handle lever so that any extra application of force is not transmitted to the jaws. More specifically, the present invention comprises surgical instrument with a body having a drive shaft extending along a longitudinal axis and coupled to a pair of jaws that are moveable between an open and a closed position, a bearing tube secured around the drive shaft for movement therewith and having a stop extending therefrom, a pair of tracks defined in the body and extending obliquely to the longitudinal axis, a lever having an upper end pivotally coupled to the body by a pivot pin positioned in the pair of tracks, a lower end that extends out of the body, and an intermediate portion that is engaged with the stop of the bearing tube, and a spring assembly positioned in the body and having a bearing surface that is biased to urge the pivot pin into a first end of the tracks. The lever may comprise a fork having a pair of opposing tines with a pair of holes formed therethrough, respectively, that accept the pivot pin. The intermediate portion of the lever may include a pair of inner bearing surfaces that are engaged with the stop of the bearing tube. The inner bearing surfaces may be curved. The lever may be pivotal about the pivot pin from a first position, where the bearing tube positions the drive shaft so that the jaws are in the open position, to a second position, where the bearing tube positions the drive shaft so that the jaws are in the closed position. The lever may be pivotal about the intermediate portion into a third position where the pivot pin has moved from the first end of the track toward the second end of the track against the bias of the spring assembly. The spring assembly may comprise a spring holder secured within the body. The spring holder may comprise a ferrule and a flange extending from the ferrule. The spring assembly may comprise a spring having a first end at least partially positioned about the ferrule. The spring assembly may comprise a plunger extending from a second end of the spring and having a pin engaging surface abutting the pivot pin. The spring may be pre-loaded to prevent movement of the pivot pin until the lever is in the second position.

The present invention also comprises a method of limiting the force applied to a surgical instrument. A first step comprises providing a body having a drive shaft extending along a longitudinal axis and coupled to a pair of jaws that are moveable between an open and a closed position, a bearing tube secured around the drive shaft for movement therewith and having a stop extending therefrom, a pair of tracks defined in the body and extending obliquely to the longitudinal axis, a lever having an upper end pivotally coupled to the body by a pivot pin positioned in the pair of tracks, a lower end that extends out of the body, and an intermediate portion that is engaged with the stop of the bearing tube, and a spring assembly positioned in the body and having a bearing surface that is biased to urge the pivot pin into a first end of the tracks. Another step comprises actuating the lever to move the lever from the first position to the second so that the jaws are moved to the closed position. A further step comprises continuing to actuate the lever so that the lever pivots about the intermediate portion and the pivot pin moves along the tracks.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 7A is an isometric view of a lever for a handle assembly according to the present invention;

FIG. 7B is a side view of a lever for a handle assembly according to the present invention;

DETAILED DESCRIPTION OF THE INVENTION

Figure 1:
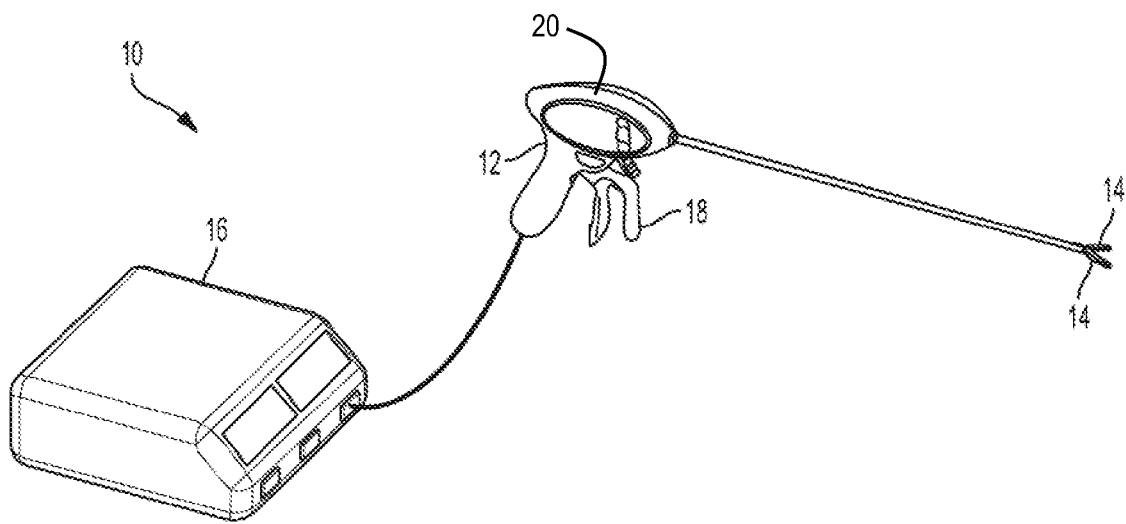
FIG. 1 is a schematic of an electrosurgical system having a pair of jaws carrying electrodes for electrosurgically treating tissue

Referring to the figures, wherein like numeral refer to like parts throughout, there is seen in FIG. 1 a vessel sealing system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaw 14. The dimensions of jaws 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a lever 18 extending from the main body 20 of sealer 12.

Figure 2:
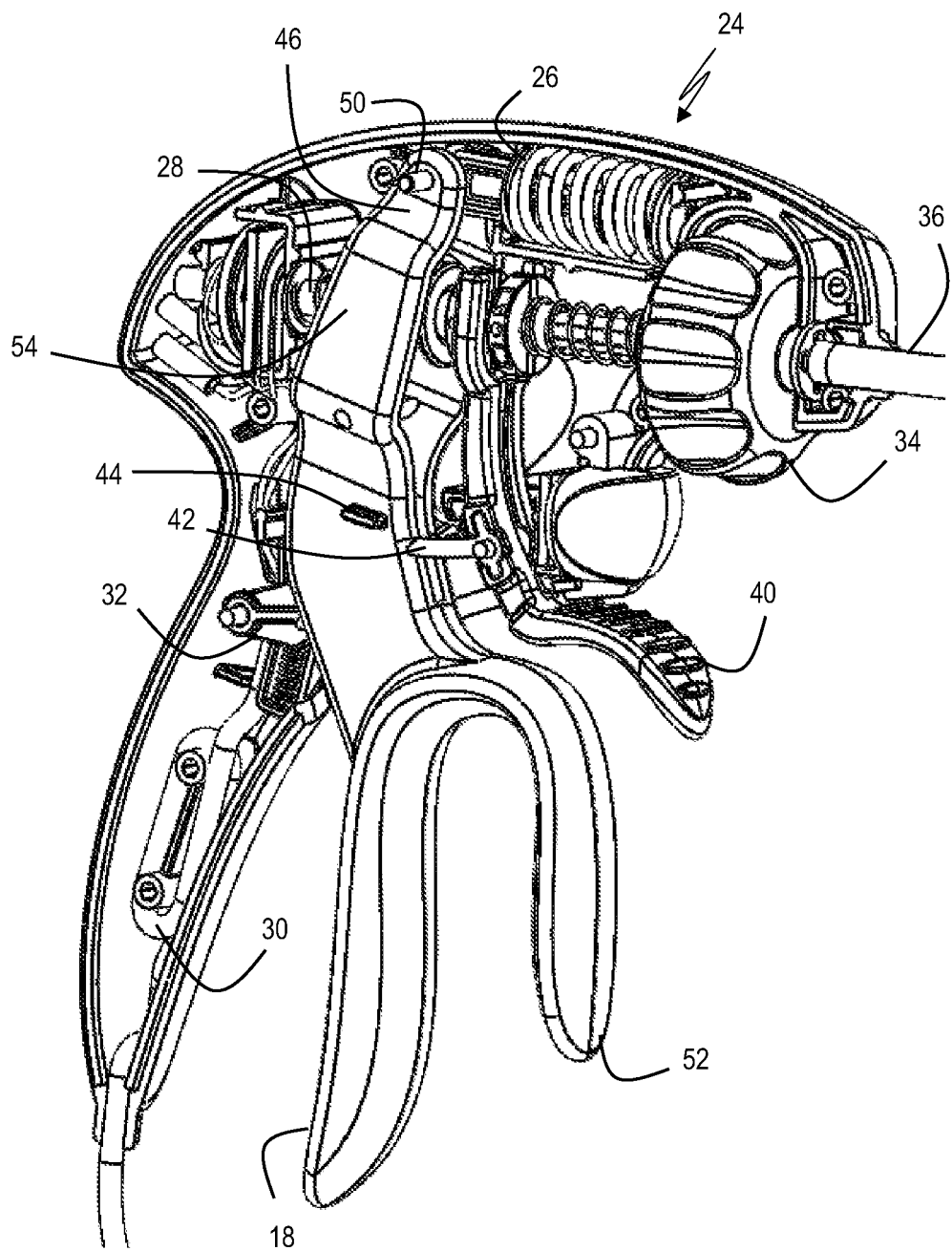
FIG. 2 is an isometric view of the components of a handle assembly for an electrosurgical vessel sealer according to the present invention.
Figure 3:
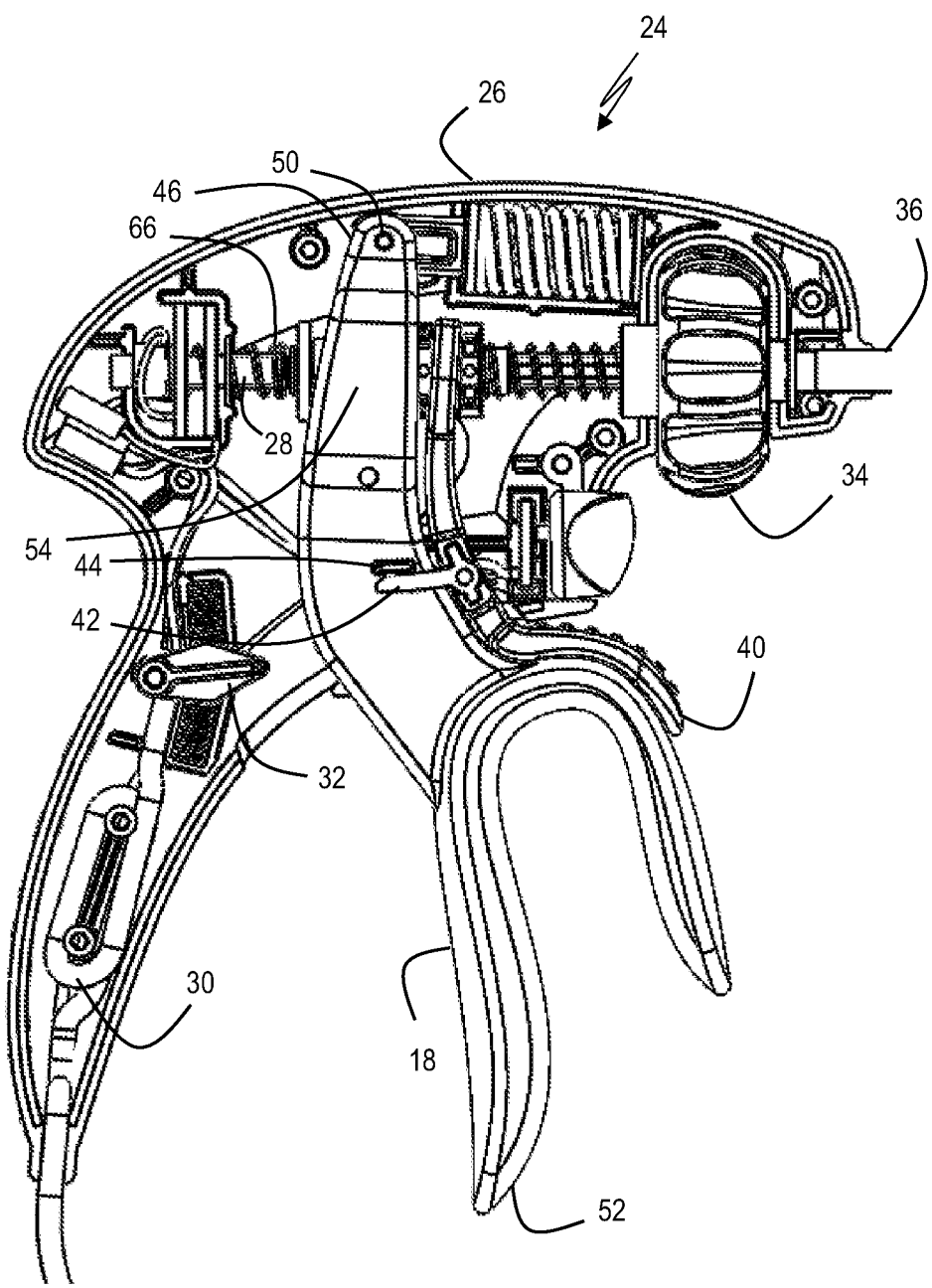
FIG. 3 is a front view of the components of a partially disassembled handle assembly for an electrosurgical vessel sealer according to the present invention.

Referring to FIGS. 2 and 3, vessel sealer 12 includes a handle assembly 24 comprised of a housing body 26 that encloses a drive shaft 28. Drive shaft 28 is coupled to jaws 14 so that longitudinal movement of drive shaft 28 will mechanically move jaws 14 between the open and closed positioned. Housing body 26 also encloses cabling 30 for delivering energy to jaws 14 as well as a latching mechanism 32 for selectively retaining lever 18 when it is moved from a first position, where jaws 14 are open, to a second position, where jaws 14 are closed. Housing body 26 partially encloses a knob 34 that is coupled to an outer shaft 36 that surrounds drive shaft 28 and supports jaws 14 such that rotation of knob 34 will rotate jaws 14 through 360 degrees. Handle assembly 24 further comprises a knife trigger 40 for extending a blade (not shown) between jaws 14 to sever a treated vessel. Knife trigger 40 may include an interlock 42 engaged with a tab 44 mounted to lever 18 to prevent operation of knife trigger 40 until lever 18 has been moved into the second position to free interlock 42 when jaws 14 are closed Drive shaft 28 is coupled to lever 18 so that movement of lever 18 between its open and closed positions correspondingly moves jaws 14 between their open and closed positions. More specifically, lever 18 is pivotally mounted to housing body 26 at an upper end 46 by a lever pivot pin 50. Lever 18 extends from upper end 46 to a lower end 52 that projects out of housing body 26 for grasping by a user. An intermediate portion 54 of lever 18 is captured within a lever bearing tube 56 that is secured to drive shaft 28.

Figure 4:
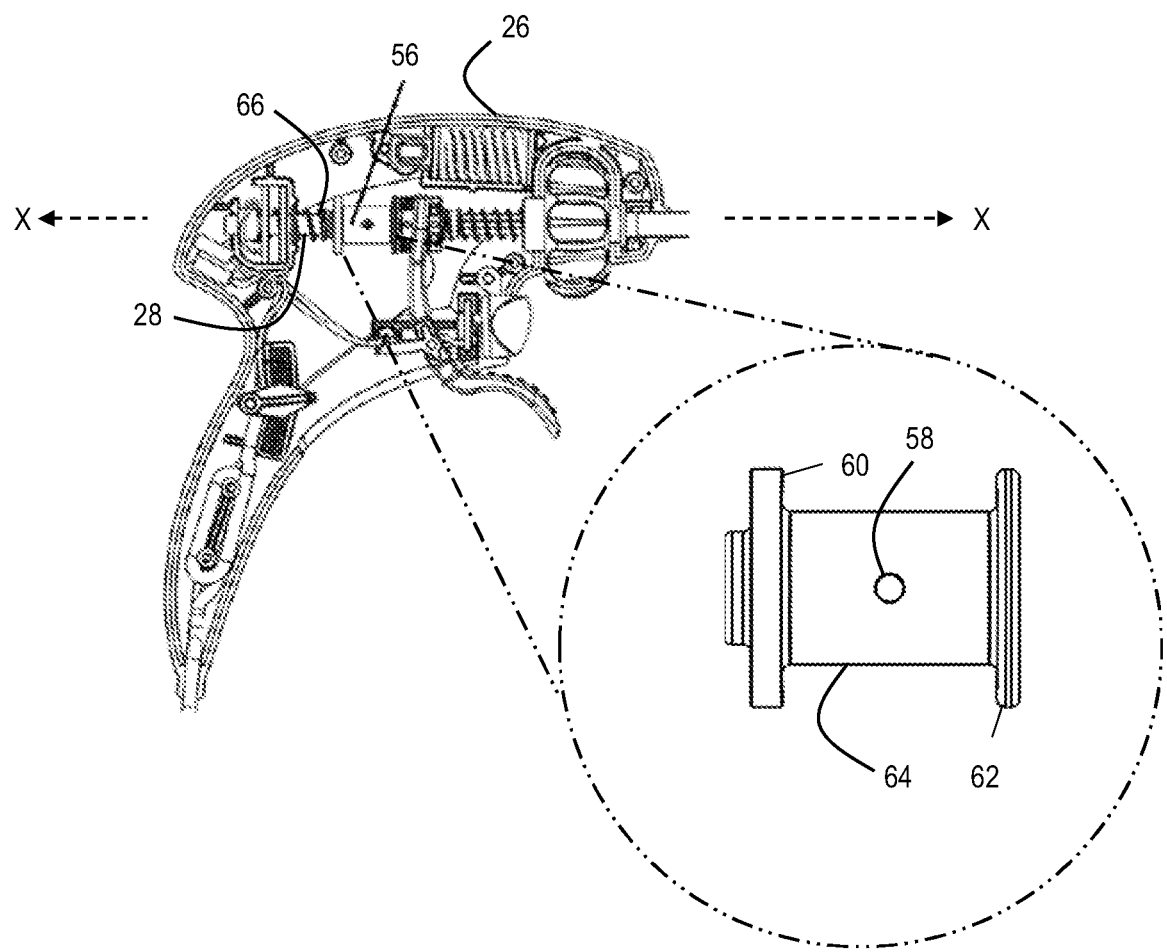
FIG. 4 is a front view of a partially disassembled handle assembly including an enlargement of a lever bearing tube according to the present invention.

Referring to FIG. 4, lever bearing tube 56 has a cylindrical body 58 that extends between a proximal stop 60 and a distal stop 62. Lever bearing tube 56 is secured to drive shaft 28, such as by a pin 64 extending therebetween, so that movement of lever bearing tube 56 by lever 18 causes longitudinal translation of drive shaft 28 and thus opening and closing of jaws 14. A return spring 66 is positioned about drive shaft 28 and biases lever bearing tube 56 into a distal position set by distal stop 62. The distal position of lever bearing tube 56 positions drive shaft 28 so that the jaws 14 are in the open position, and the proximal position of lever bearing tube 56 positions drive shaft 28 so that the jaws 14 are in the closed position. Return spring 66 biases lever bearing tube 56 so that jaws 14 are in the open position in absence of any force being applied by lever 18. Movement of lever 18 from the open to the closed position will move lever bearing tube 56 so that jaws 14 are driven from the open to the closed position.

Figure 5:
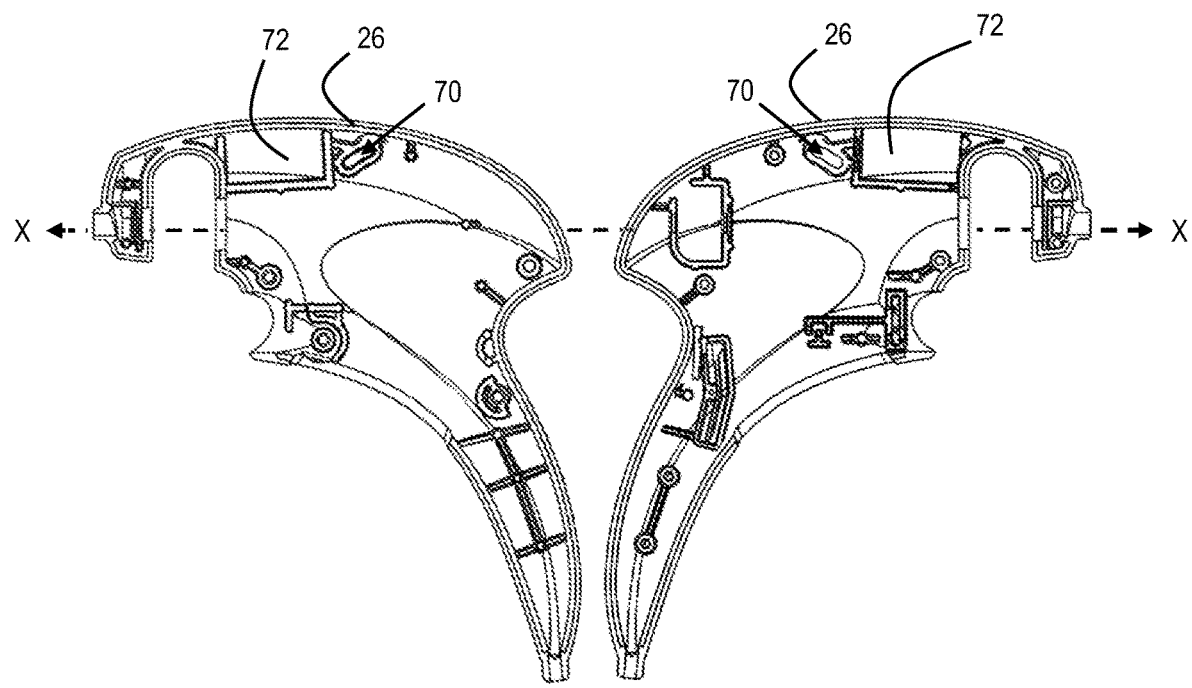
FIG. 5 is a front view of a handle body showing a lever pin track according to the present invention.

Referring to FIG. 5, lever pivot pin 50 is positioned in a track 70 formed by housing body 26. Housing body 56 is shown as formed from two opposing body halves such that track 70 is formed on both opposing housing body 26, and thus comprises a pair of opposing tracks 70 on either side of a plane defined by longitudinal axis X-X for capturing the opposing ends of pivot pin 50. Tracks 70 extends obliquely to the longitudinal axis X-X of housing body 26 and is positioned proximately to a spring assembly holder 72 formed by housing body 26. Tracks 70 are configured to allow lever pivot pin 50 to slide therein when lever 18 is moved by a user past the fully closed position of jaws 14, thereby limiting the amount of force applied by lever 18 to jaws 14. As explained below, movement of lever 18 beyond its closed position will result in lever 18 pivoting around its intermediate portion 54. As a result, tracks 70 are oriented to allow lever pivot pin 50 to rotate with lever 18.

Figure 6A:
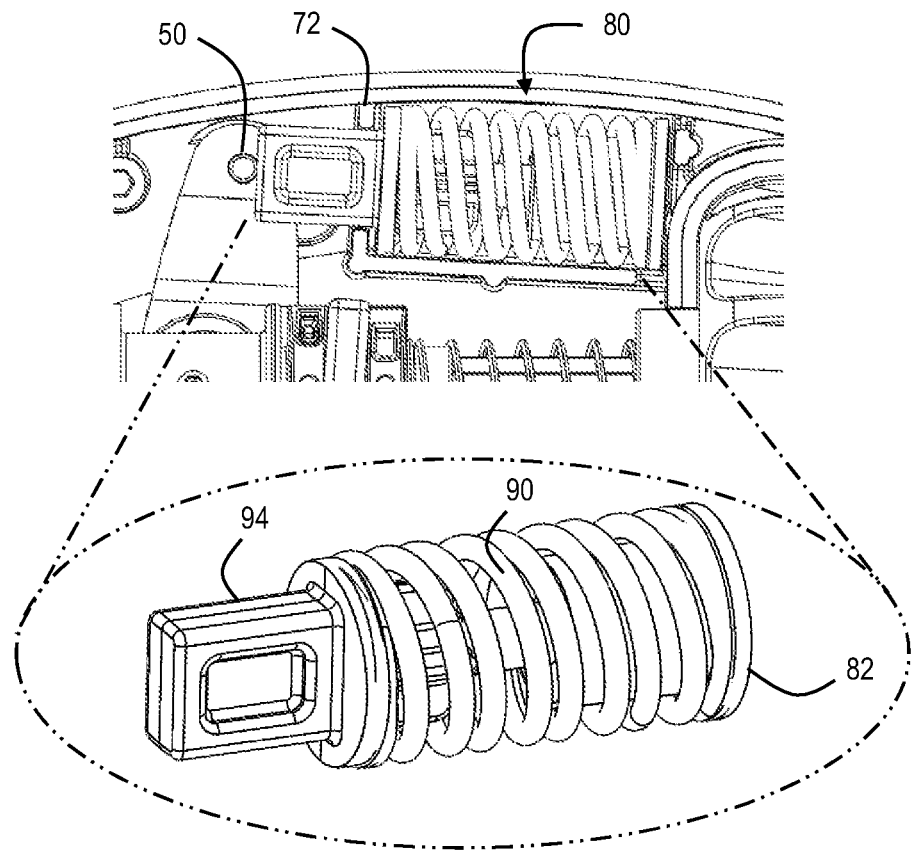
FIG. 6A is a partial front view of a disassembled handle assembly including an enlargement of a spring assembly according to the present invention.
Figure 6B:
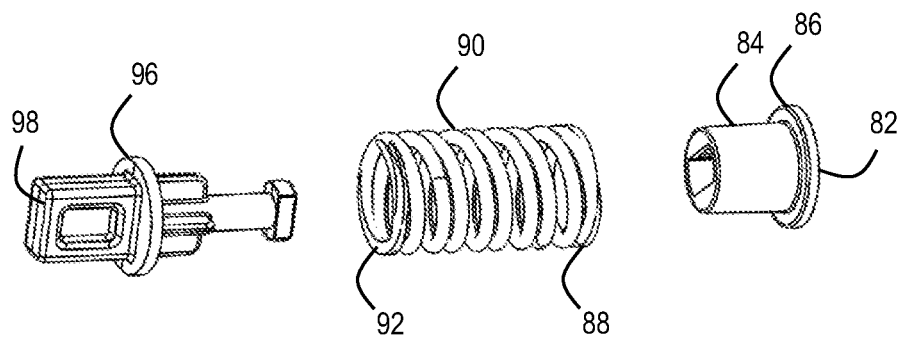
FIG. 6B is an explored view of a spring assembly according to the present invention.

Referring to FIGS. 6A and 6B, a spring assembly 80 is positioned in spring assembly holder 72 of housing body 26 proximately to tracks 70. Spring assembly 80 comprises a spring holder 82 having a ferrule 84 and a flange 86. Spring holder 82 accepts a first end 88 of a spring 90 for securing spring 90 and spring assembly 80 in spring assembly holder 72 of housing body 26. A second end 92 of spring 90 is in engagement with a plunger 94 having a flange 96 abutting second end 92 of spring 90 and a pin bearing surface 98 for engaging lever pivot pin 50. When mounted in spring assembly holder 72 of housing body 26, spring 90 is partially loaded and positioned so that pin bearing surface 98 will engage lever pivot pin 50 and apply a biasing force pushing lever pivot pin 50 toward the proximal end of track 70. As a result, lever pivot pin 50 will be held in the proximate end of tracks 70 of housing body 26 until a force is applied by lever 18 to pivot pin 50 overcomes the bias of spring 90. Spring 90 is therefore configured to become further compressed is response to a predetermined amount of force being applied to pivot pin 50. As explained below, rotation of lever 18 about its intermediate portion 54 after lever 18 and jaws 14 have reached the closed position will provide in this force and result in pivot pin 50 moving distilling within tracks 70 against the bias of spring 90.

Referring to FIGS. 7A and 7B, lever 18 is configured as a fork 100 that extends in two tines 102 and 104 that define the intermediate portion 54 and upper end 46 of lever 18. Fork 100 extends around lever bearing tube 56 and includes curved inner bearing surfaces 106 and 108. Curved inner bearing surfaces 106 and 108 engage proximal stop 60 of lever bearing tube 56 to apply a force that moves lever bearing tube 56 longitudinally and to create a new pivot point for lever 18 when lever 18 is actuated beyond the closed position. Tines 102 and 104 terminate in opposing upper ends 110 and 112 that include holes 114 and 116 formed therethrough, respectively. Holes 114 and 116 accept lever pivot pin 50 and pivotally couple lever 18 to housing body 26 via lever pivot pin 50 riding within tracks 70.

Figure 8:
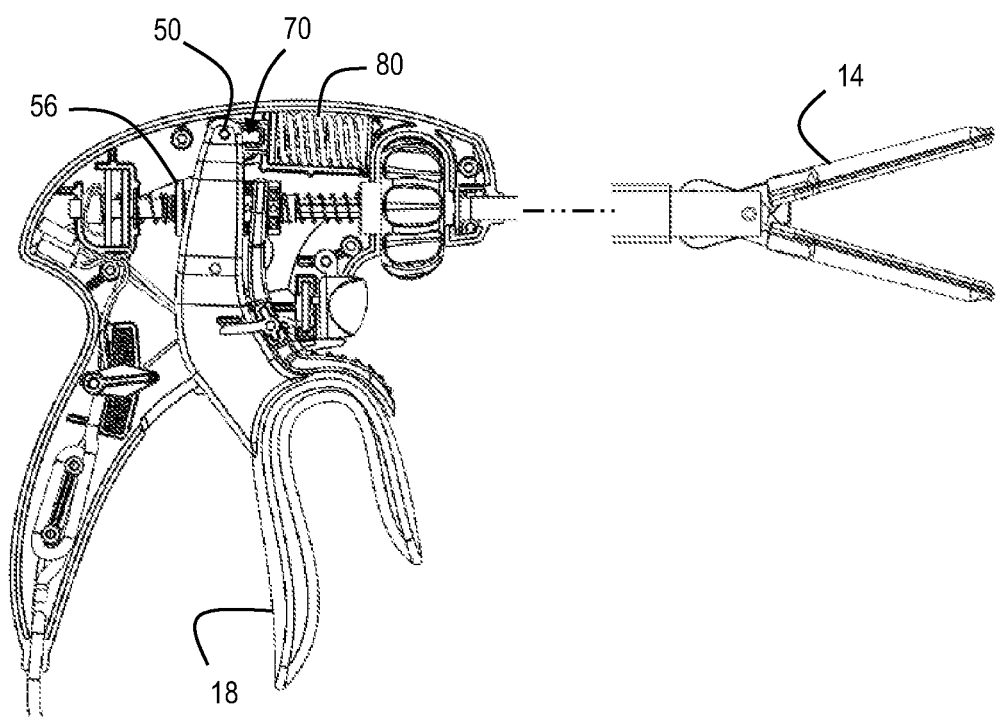
FIG. 8 is a front view of the handle assembly when the jaws of the electrosurgical vessel sealer are in the open position.

Referring to FIG. 8, jaws 14 of vessel sealer are open when lever 18 is in the open position. In this position, lever bearing tube 56 is in its distal most location so that drive shaft 28 has translated longitudinally so that drive shaft 28 has fully opened jaws 14. Lever pivot pin 50 is held in the proximal end of tracks 70 due to the pre-load force applied by spring assembly 80.

Figure 9:
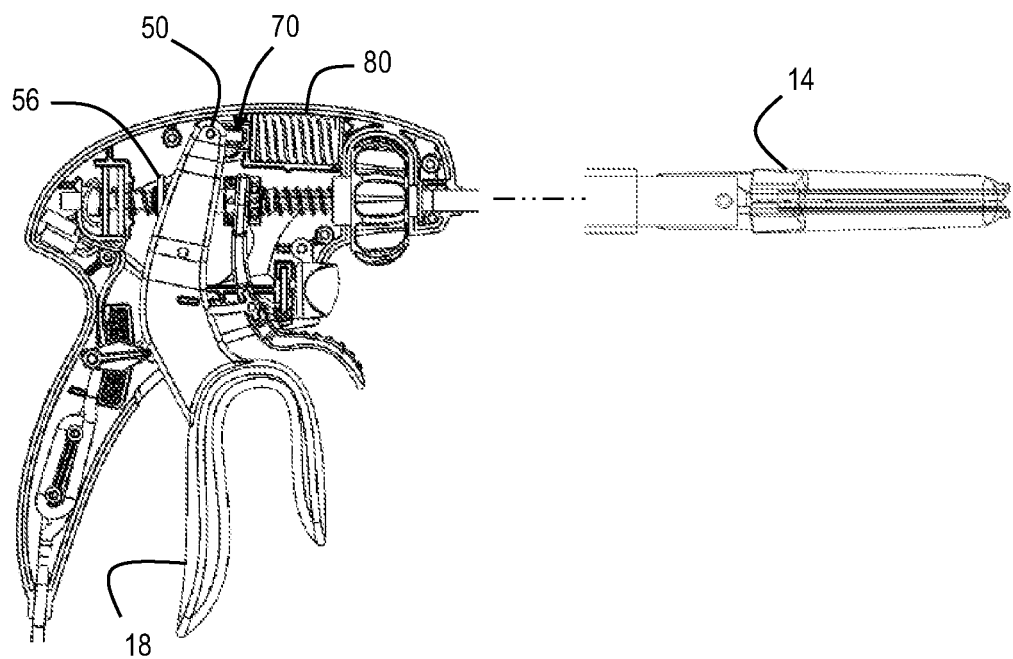
FIG. 9 is a front view of handle assembly when the jaws of the electrosurgical vessel sealer are in the closed position.

Referring to FIG. 9, movement of lever 18 into the second position, such as by a user, pulls lever bearing tube 56 proximally along the longitudinal axis X-X, thereby moving drive shaft 28 longitudinally and closing close jaws 14. Lever pivot pin 50 remains in the proximate end of tracks 70 as the force supplied by the pre-load of spring assembly is configured to provide enough force to keep lever pivot pin 50 in place while lever 18 is pivoted into the closed position. As jaws 14 full close, lever bearing tube 56 and proximal stop 60 are not capable of further proximal longitudinal movement and lever 18 and jaws 14 are in the fully closed position.

Figure 10:
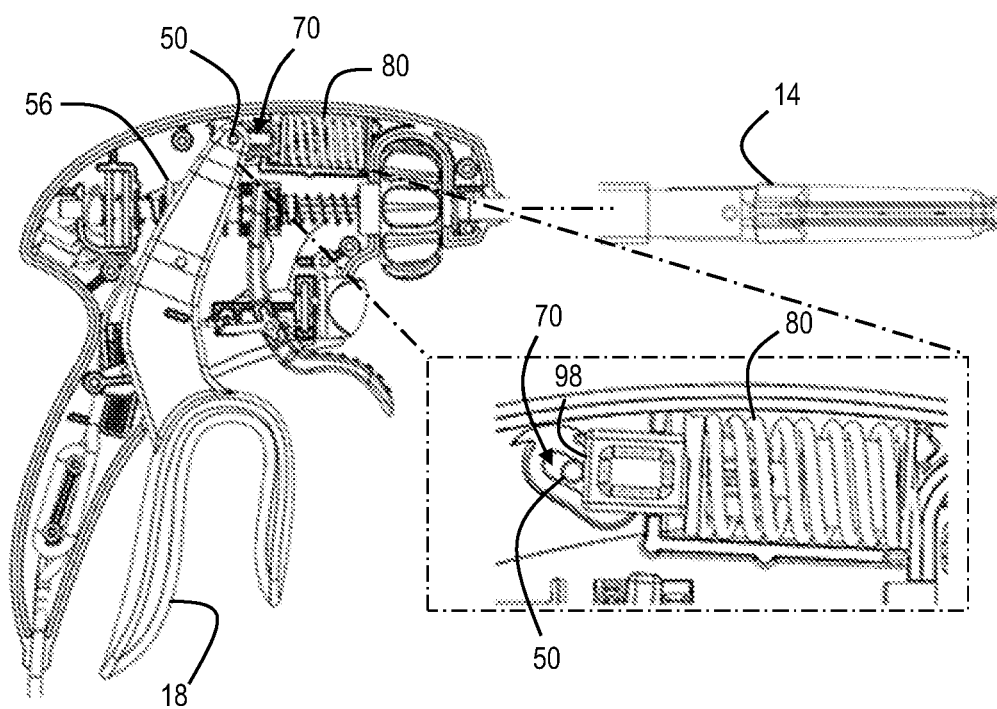
FIG. 10 is a front view of the handle assembly when the jaws of the electrosurgical vessel sealer are in the fixed position.

Referring to FIG. 10, additional movement of lever 18 beyond the second, closed position where jaws 14 are fully closed results in lever 18 moving into a flexed state where no further force is imparted to lever bearing tube 56 or jaws 14. As lever bearing tube 56 has reached its most proximal position, the further application of force to lever 18 will cause lever 18 to pivot about its intermediate portion 54 where curved bearing surfaces 106 and 108 engage proximal stop 60 of lever bearing tube 56. Pivoting of lever 18 about its intermediate portion 54 imparts a force to lever pivot pin 50 via upper ends 110 and 112 that drives lever pivot pin 50 distally in tracks 70 against pin bearing surface 98 of spring assembly 80. If lever 18 is continues to be squeezed past the fully closed position, the pre-load of spring 90 will be overcome and lever pivot pin 50 will slide distally within tracks 70 as lever 18 beings to rotate about the new pivot point created by bearing surfaces 106 and 108 and proximal stop 60. As a result of lever 18 pivoting about the new pivot point created by bearing surfaces 106 and 108 and proximal stop 60, lever 18 will not apply any longitudinal forces to lever bearing tube 56 that could over-compress of jaws 14 or damage vessel sealer 12. Lever 18 will instead continue to rotate about the new pivot point such that lever pivot pin 50 is moved along tracks 70 against the bias of spring 90. Lever 18 is thus effectively decoupled from jaws 14 so that movement of lever 18 beyond the closed position will not apply any additional closing force to jaws 14 and lever 18 will rotate into the flexed position without applying any more force to drive shaft 28 via lever bearing 58.

The present invention thus provides an approach that limits the amount of force that a user can apply to the jaws of vessel sealer 12. As a result, the present invention helps controls seal quality by limiting the pressure applied to, and thus, the thickness of the clamped tissue. Controlling the clamped thickness reduces over-desiccation, low burst pressure seals, charring and the potential for cutting through the compressed tissue. The present invention also reduces potential for tissue tearing by limiting the tissue gripping force, i.e., tissue is inclined to slip versus tearing if user applies excessive organ manipulation force.

What is claimed is:

1. A surgical instrument, comprising:
   a body having a drive shaft extending along a longitudinal axis and coupled to a pair of jaws that are moveable between an open and a closed position;
   a bearing tube secured around the drive shaft for movement therewith and having a stop extending therefrom;
   a pair of tracks positioned on opposing side of a plane defined by the longitudinal axis and extending obliquely to the longitudinal axis;
   a lever having an upper end pivotally coupled to the body by a pivot pin positioned in the pair of tracks, a lower end that extends out of the body, and an intermediate portion having a pair of curved inner bearing surfaces that are engaged with the stop of the bearing tube, wherein the lever comprises a fork having a pair of opposing tines with a pair of holes formed therethrough, respectively, that accept the pivot pin and wherein the lever is pivotal about the pivot pin from a first position, where the bearing tube positions the drive shaft so that the pair of jaws are in the open position, to a second position, where the bearing tube positions the drive shaft so that the pair of jaws are in the closed position; and
   a spring assembly comprising a spring holder having a ferrule and a flange extending from the ferrule secured within the body and having a bearing surface that is biased to urge the pivot pin into a first end of the pair of tracks, wherein the lever is pivotal about the intermediate portion into a third position where the pivot pin has moved from the first end of the pair of tracks toward the second end of the pair of tracks against the bias of the spring assembly.

2. The surgical instrument of claim 1, wherein the spring assembly comprises a spring having one end at least partially positioned about the ferrule.

3. The surgical instrument of claim 2, wherein the spring assembly comprises a plunger extending from another end of the spring and including a surface abutting the pivot pin.

4. The surgical instrument of claim 3, wherein the spring is pre-loaded to prevent movement of the pivot pin until the lever is in the second position.

5. A method of limiting an amount of force applied to a surgical instrument, comprises the steps of:
   providing a body having a drive shaft extending along a longitudinal axis and coupled to a pair of jaws that are moveable between an open and a closed position, a bearing tube secured around the drive shaft for movement therewith and having a stop extending therefrom, a pair of tracks defined in the body and extending obliquely to the longitudinal axis, a lever having an upper end pivotally coupled to the body by a pivot pin positioned in the pair of tracks, a lower end that extends out of the body, and an intermediate portion that is engaged with the stop of the bearing tube, and a spring assembly positioned in the body and having a bearing surface that is biased to urge the pivot pin into a first end of the pair of tracks wherein the lever comprises a fork having a pair of opposing tines with a pair of holes formed therethrough, respectively, that accept the pivot pin, wherein the intermediate portion of the lever includes a pair of curved inner bearing surfaces that are engaged with the stop of the bearing tube, and wherein the spring assembly comprises a spring holder secured within the body and supporting a spring that biases a plunger having a surface into the pivot pin;
   actuating the lever to move the lever from the first position to the second position so that the jaws are moved to the closed position; and
   continuing to actuate the lever into a third position so that the lever pivots about the intermediate portion while the pivot pin moves along the pair of tracks.

* * * * *